United States Patent
Engler et al.

(10) Patent No.: US 6,519,034 B1
(45) Date of Patent: Feb. 11, 2003

(54) OIL QUALITY SENSOR

(75) Inventors: Kevin J. Engler, Freeport, IL (US); Thomas R. Giuffre, Freeport, IL (US); Gary R. O'Brien, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/212,233

(22) Filed: Dec. 16, 1998

(51) Int. Cl.⁷ .................. G01N 21/00; G01N 15/06
(52) U.S. Cl. .................. 356/338; 356/342; 356/343; 250/574
(58) Field of Search .................. 356/338, 339, 356/342, 343, 335, 336, 432, 436, 441, 442; 250/461.1, 573, 574, 575

(56) References Cited

U.S. PATENT DOCUMENTS

| | | | |
|---|---|---|---|
| 4,198,161 A | 4/1980 | Larson | 356/339 |
| 5,291,626 A | 3/1994 | Molnar et al. | 8/158 |
| 5,408,307 A * | 4/1995 | Yamamoto et al. | 356/73 |
| 5,489,977 A * | 2/1996 | Winslow et al. | 356/73 |
| 5,565,984 A * | 10/1996 | Girvin | 356/336 |
| 5,589,935 A | 12/1996 | Biard | 356/339 |
| 5,604,590 A * | 2/1997 | Cooper et al. | 356/338 |
| RE35,566 E | 7/1997 | Boyer et al. | 356/72 |
| 5,729,025 A | 3/1998 | Erickson et al. | 250/574 |
| 5,828,458 A | 10/1998 | Taylor et al. | 356/440 |
| 5,872,361 A | 2/1999 | Paoli et al. | 250/341.8 |
| 5,881,578 A | 3/1999 | Proppe et al. | 68/12.02 |
| 5,889,192 A | 3/1999 | Engel | 73/1.02 |
| 5,923,433 A | 7/1999 | Giuffre et al. | 356/440 |
| 5,957,144 A | 9/1999 | Neff et al. | 134/56 |
| 6,007,640 A | 12/1999 | Neff et al. | 134/18 |
| 6,141,097 A | 10/2000 | Herman | 356/335 |

* cited by examiner

*Primary Examiner*—Michael P. Stafira
(74) *Attorney, Agent, or Firm*—Kris T. Fredrick

(57) ABSTRACT

A fluid quality sensor system comprising a light source, a first light sensitive element disposed at a distance from the light source, forming a gap having dimensions suitable for permitting a fluid to flow therebetween, and aligned with the light source to receive light transmitted by the light source through the fluid, a second light sensitive element disposed perpendicular to a midpoint of a light path between the light source and the first light sensitive element, and a third light sensitive element disposed so as to form an acute angle at the midpoint with the light source.

14 Claims, 3 Drawing Sheets

OIL QUALITY SENSOR

BACKGROUND OF THE INVENTION

1. Field of the Invention

This invention relates to an apparatus and method for determining the quality of a fluid, such as engine or transmission oil. More particularly, this invention relates to a method and apparatus for determining the quality of oil using turbidity sensing technology.

2. Description of Related Art

The rising cost of highly complex engine and transmission repair, for example, in the earth moving equipment business, has generated a market interest for affordable transmission oil sensing. There has always been a significant interest in measuring oil quality to gain better control of viscosity breakdown and contamination from water or antifreeze or contaminants such as metal, dust, carbon, etc. The use of low cost oil quality sensing from a preventive maintenance perspective is highly desirable for reducing expensive equipment upkeep costs and obtaining better control of preventive maintenance scheduling.

Turbidity sensors are used in many different types of applications. Some turbidity sensors are used in association with machines for washing articles, such as dishwashers and washing machines. Most turbidity sensors measure the effect on a light beam by particulate matter suspended within a fluid. Some turbidity sensors use only a transmitted light signal while others use both scattered and transmitted light signals.

U.S. Pat. No 4,198,161 to Larson teaches a low turbidity nephelometer which measures the turbidity of a water sample by directing a beam of light into the sample and sensing the light scattered from particles of turbidity suspended in the water. When low levels of turbidity are sought to be sensed, the presence of stray light in the instrument becomes more and more critical. The nephelometer, which is designed to reduce the affects of stray light, comprises a transport cell for containing a liquid sample, a light source, and a detector, whereby the cell is characterized in that either the illuminating light beam or the detected light passes through the cell wall face at an acute angle to the normal to the cell wall face.

U.S. Pat. No. 5,589,935 to Biard teaches a turbidity sensor having two light sensitive components, one of which is displaced from a light source, such as a light emitting diode, so that a fluid can pass therebetween, and the other of which is disposed within a common compartment with the light source so that it can measure the intensity of light provided by the light source. A regulator is provided to control the magnitude of current provided to the light source so that its light intensity can be regulated. In this way, the intensity of light emitted by the light source, such as a light emitting diode, can be controlled regardless of the aging of the LED, the variability of LED characteristics and the temperature surrounding the LED. The constant light emission from the light source permits the other light sensitive component to be used as a reliable indication of the turbidity of the solution passing between the light source and the first light sensitive component.

One problem with conventional turbidity sensing systems is the occurrence of scattered signal foldback. Scattered signal foldback occurs when the fluid under evaluation is so turbid that light scattered from the light source cannot make it to the light detector due to further internal scattering, the result of which is a reduction in the effectiveness of the signal.

SUMMARY OF THE INVENTION

It is one object of this invention to provide an affordable sensing system for determining the quality of a fluid, such as engine or transmission oil.

It is another object of this invention to provide a system for turbidity sensing which overcomes the ineffectiveness of conventional turbidity sensing systems due to scattered signal foldback.

It is yet another object of this invention to provide a turbidity sensing system suitable for determining oil quality.

These and other objects of this invention are achieved by a fluid quality sensor system comprising a light source, a first light sensitive element disposed at a distance from the light source, forming a gap having dimensions suitable for permitting a fluid to flow therebetween, which first light sensitive element is aligned with the light source to receive light transmitted by the light source through the fluid, a second light sensitive element disposed substantially perpendicular to an approximate midpoint of a light path between the light source and the first light sensitive element, and a third light sensitive element disposed so as to form an acute angle at the approximate midpoint of the light path with respect to the light source.

The method for determining the quality of a liquid such as engine or transmission oil in accordance with one embodiment of this invention comprises the steps of transmitting a light beam into the oil from a light source, measuring the amount of light at three points peripheral to the oil, and determining the quality of the oil based upon the measured amounts of light. The three points for measurement of the light are directly across from the light source at which point the amount of transmitted light is measured, a point substantially perpendicular to the approximate midpoint of the transmitted light at which point the amount of perpendicular light scatter is measured, and a point which forms an acute angle at the midpoint of the transmitted light with respect to the light source at which point the amount of back scatter light is measured.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

Figure 1:
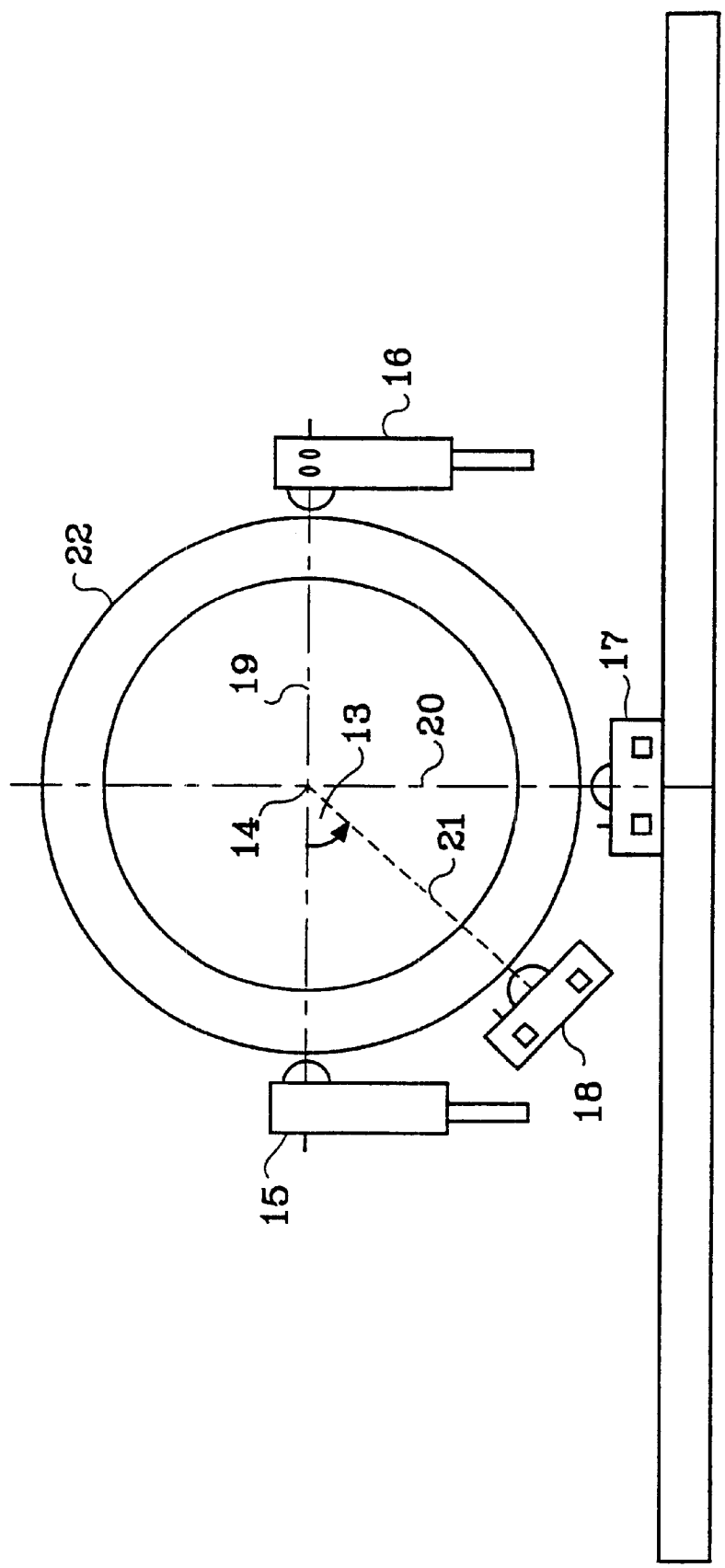
FIG. 1 is a schematic diagram of a fluid quality sensor system in accordance with one embodiment of this invention.

The method and apparatus of this invention use turbidity sensing technology with modified close geometry optics, different from standard ratio configurations, in order to determine the quality of a fluid such as engine or transmission oil. A fluid quality sensor in accordance with one embodiment of this invention is shown in FIG. 1 and comprises light source 15 and a first light sensitive element 16 disposed at a distance from light source 15 and forming a gap having dimensions suitable for permitting a fluid to flow therebetween. First light sensitive element 16 is aligned with light source 15 to receive light transmitted by light source 15 through the fluid as represented by transmitted light path 19. A second light sensitive element 17 is disposed substantially perpendicular to an approximate midpoint 14 of transmitted light path 19 between light source 15 and first light sensitive element 16. By the phrase "substantially perpendicular to an approximate midpoint" of the transmitted light path, it will be understood by those skilled in the art that precise perpendicularity to the precise midpoint of the transmitted light path of the second light sensitive element 17 is not required. A third light sensitive element 18 is disposed so as to form an acute angle 13 at midpoint 14 with respect to light source 15. In accordance with one preferred embodiment of this invention, acute angle 13 is less than about 48 degrees. It may, however, also be greater than 48 degrees.

Disposed within the gap formed by light source 15 and first light sensitive element 16, in accordance with one preferred embodiment of this invention, is flow tube 22 through which the fluid, the quality of which is being determined by the fluid quality sensor system of this invention, is flowing. It will be apparent to the artisan of ordinary skill in the art that the system of this invention may be constructed and arranged to accommodate other oil containing arrangements, such as an oil pan or sump, within the gap formed by light source 15 and first light sensitive element 16.

In accordance with the method of this invention for determining the quality of a fluid, light is transmitted by light source 15 into the liquid flowing through flow tube 22 and the amount of transmitted light, represented by transmitted light path 19, is measured by first light sensitive element 16. The amount of perpendicular light scatter 20 is measured by second light sensitive element 17 and the amount of back scatter light 21 is measured by third light sensitive element 18. Based upon the measured amounts of transmitted light 19, perpendicular light scatter 20, and back scatter light 21, the turbidity of the fluid is determined, which, in turn, is used for determining the quality of the fluid.

Two unique aspects are provided by the system and method of this invention. First, we are able to generate useful turbidity data without scattered signal foldback which is typical of conventional systems at extremely high turbidity levels. As previously indicated, scattered signal foldback occurs when the fluid under evaluation is so turbid that light scattered from the light source cannot penetrate through the fluid to the detector due to absorption and /or internal scattering of the light within the fluid, thereby violating the normal relationship between turbidity and the scattered signal, i.e. the higher the turbidity, the higher the scattered signal. Secondly, using the system and method of this invention, in particular, the back scatter light optical geometry, we are able to distinguish, for example, between virgin oil and oil contaminated with water and antifreeze (ethylene glycol). These two aspects of the fluid quality sensor system of this invention permit the system to perform well as a ratio turbidity detector while also providing indications of contamination.

Suitable light sources for use in the system of this invention may include infrared light emitting diodes (LED), standard red LED's, laser diodes, incandescent sources, and white light LED's. Suitable light sensitive elements may include photodiodes and phototransistors.

EXAMPLE

A prototype of the fluid quality sensor system of this invention was built and tested with mixtures of four types of oil: new oil, used oil, new oil with a 1% concentration of 50/50 mixture of water/antifreeze (W/A), and used oil with a 1% concentration of 50/50 mixture of water/antifreeze (W/A). Table 1 shows a summary of the results obtained with the prototype.

Table 1

| % Used Oil In A Solution Of Used And New Oil | Back Scatter Signal | Back Scatter Signal - With 1% W/A Contamination | Side Scatter Signal | Side Scatter Signal - With 1% W/A Contamination | Transmitted Signal | Transmitted Signal With 1% W/A Contamination | Back Scatter/ Transmitted Ratio | Back Scatter/ Transmitted Ratio With 1% W/A Contamination |
|---|---|---|---|---|---|---|---|---|
| 0 | 10,534 | 23,808 | 4,493 | 17,989 | 26,226 | 26,188 | 0.401662 | 0.90911868 |
| 25 | 14,200 | 25,601 | 3,352 | 13,051 | 26,156 | 23,052 | 0.542896 | 1.11057609 |
| 50 | 22,645 | 25,146 | 2,166 | 12,774 | 25,504 | 18,164 | 0.8879 | 1.3843867 |
| 75 | 24,984 | 25,030 | 1,116 | 7,163 | 16,059 | 10,220 | 1.555763 | 2.44911937 |
| 100 | 24,895 | 24,949 | 438 | 5,088 | 8,530 | 4,797 | 2.918523 | 5.20095893 |

Figure 2:
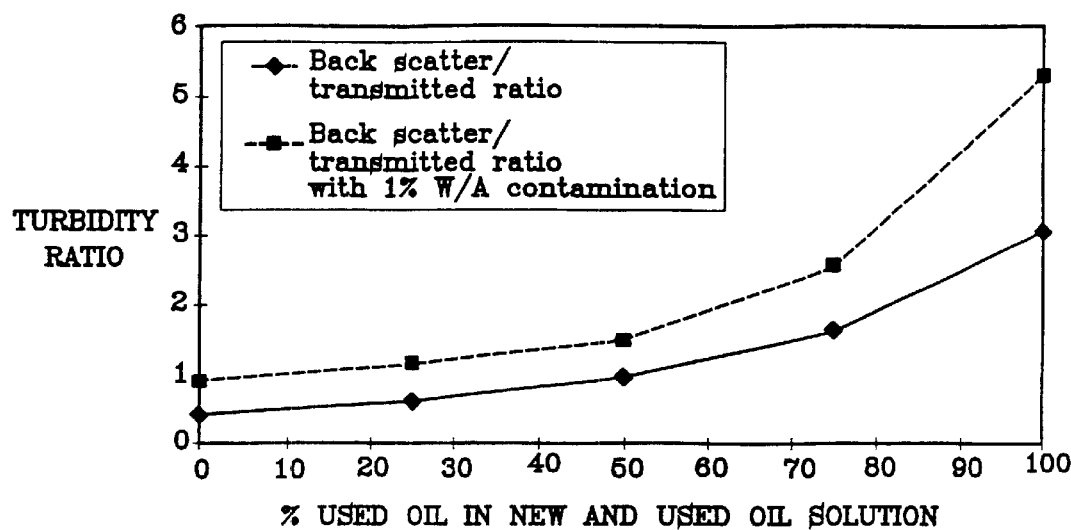
FIGS. 2 and 3 are graphic representations showing the quality of a fluid as determined by application of the fluid quality sensor and method of this invention.
Figure 3:
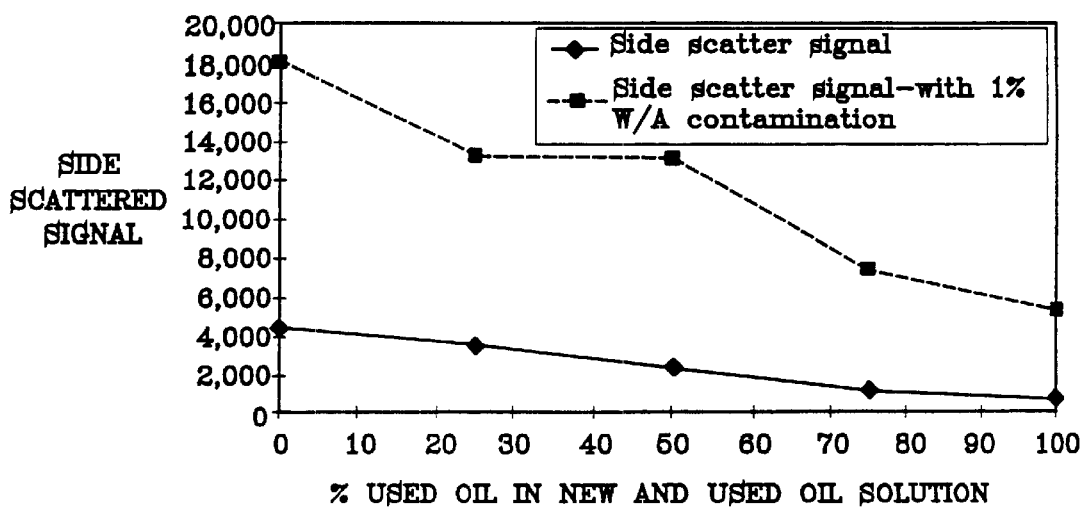
Figure 4:
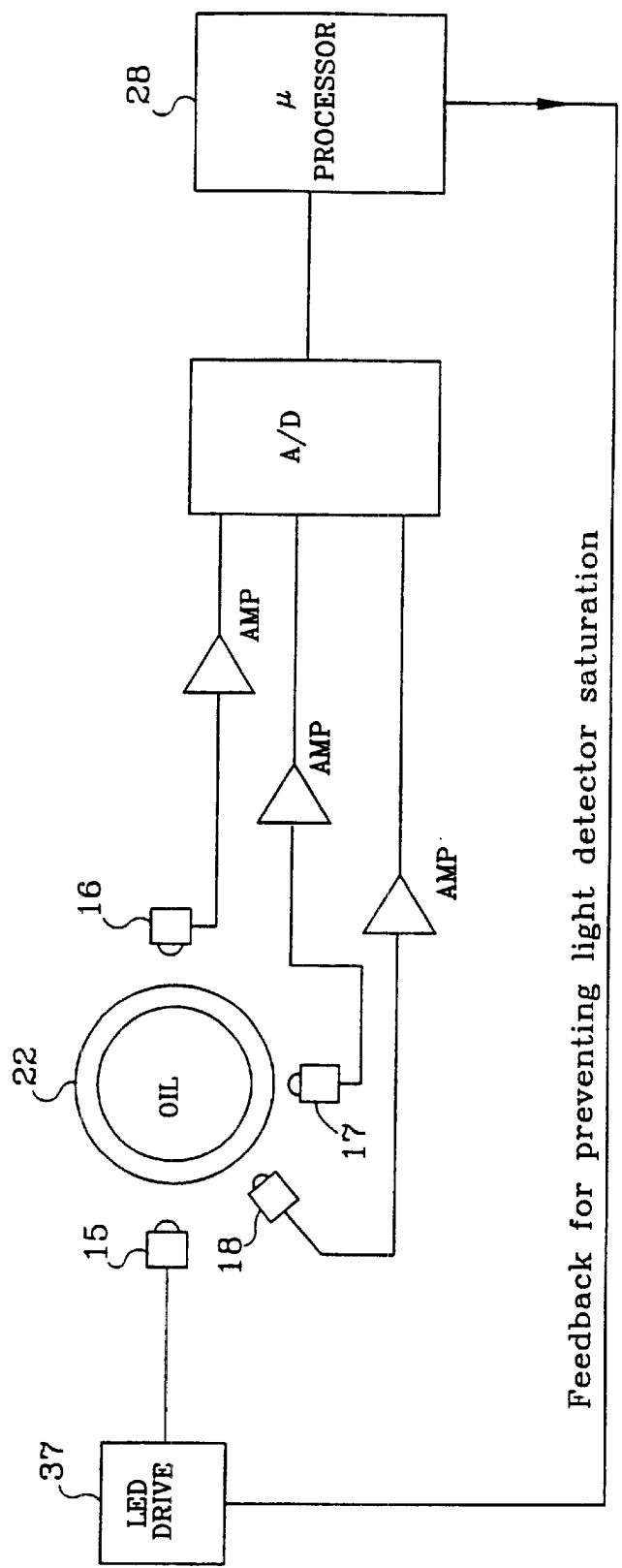
FIG. 4 is a schematic diagram of a fluid quality sensor system in accordance with another embodiment of this invention.

FIGS. 2–3 are graphical representations of the data presented in Table 1. FIG. 2 shows back scatter light/transmitted light ratios for various levels of used transmission oil with and without 1% water and antifreeze contamination and FIG. 3 shows side scatter signals for various levels of used transmission oil with and without 1% water and antifreeze contamination. Turbidity ratio, which is preferably, but not necessarily, calculated by a microprocessor 28, shown in FIG. 4, is defined as the ratio of back scatter light 21/transmitted light 19. Microprocessor 28 compares perpendicular light scatter 20 to an internal threshold dependent upon the ratio of back scatter light/transmitted light and provides a basis for determining water/antifreeze contamination. The output of microprocessor 28 can also be used to provide feedback to the light source control, for example, an LED drive 37, to prevent saturation of the light detectors. It will be apparent to those skilled in the art that a digital system is not required for this purpose and that an analog system employed.

FIG. 2 shows that the ratio of back scatter light 21 to transmitted light 19 enables a determination to be made of the relative level of degradation of oil, which progresses from new to used quality. As clearly shown, as the amount of used oil in the new and used oil solution increases, so too does the turbidity ratio. Although not shown, an equivalent graph of the ratio of perpendicular light scatter 20/transmitted light 19 does not provide this information, which is why back scatter light is necessary. Two curves are shown in FIG. 2, one for normal oil, and one for oil which is contaminated with a 1% solution of water and antifreeze in a 50/50 composition. It should be noted that, by the ratio signals alone, one cannot determine whether or not the oil has water/antifreeze contamination due to substantially common y-axis values between the two curves, thereby necessitating the gathering of perpendicular light scatter information.

FIG. 3 shows the effect of the level of oil degradation for water/antifreeze contaminated oil and normal oil on perpendicular (or side) light scatter. It can be seen that no matter what the level of degradation of the two types of oil, one can always distinguish between the regular and the contaminated oil because there are no common y-axis points between the two curves. Consequently, a perpendicular light scatter signal can be used to determine whether or not the solution is contaminated with water/antifreeze. If the ratio signal of FIG. 2 is mapped to a corresponding position on FIG. 3, one may be able to resolve how much water/antifreeze contamination exists rather than just determine that the 1% threshold of water/antifreeze contamination has been exceeded. It appears from the data that the water/contamination causes an increase in the perpendicular light scatter that does not occur from substances that are present in used oil. The substances in used oil appear to absorb light more than they scatter light.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for determining the quality of petroleum oil comprising the steps of:
    transmitting a light beam into said petroleum oil from a light source;
    measuring an amount of transmitted light at a point directly across from said light source;
    measuring an amount of perpendicular light scatter at a point substantially perpendicular to an approximate midpoint of said transmitted light;
    measuring an amount of back scatter light at a point which forms an acute angle at said approximate midpoint of said transmitted light with said light source; and
    determining turbidity of said petroleum oil based upon said measured amounts of transmitted light, perpendicular light scatter and back scatter light.

2. A method in accordance with claim 1, wherein said acute angle is less tan or equal to about 48 degrees.

3. A method in accordance with claim 1, wherein said light source is one of a laser diode and a light emitting diode (LED).

4. A method in accordance with claim 1, wherein said transmitted light, perpendicular light scatter and said back scatter light are measured by one of photodiodes and phototransistors.

5. The method in accordance with claim 1, wherein said step of determining turbidity comprises the step of determining contamination of the petroleum oil by antifreeze based upon said measured amount of perpendicular light scatter.

6. A method for determining turbidity of a liquid comprising:
    transmitting a light beam into said liquid from a light source;
    measuring an amount of transmitted light at a first point, wherein the first point is substantially directly across from said light source;
    measuring a first amount of light scatter at a second point, wherein the second point is substantially perpendicular to a line between said light source and said first point;
    measuring a second amount of light scatter at a third point, wherein the third point forms an acute angle with said line;
    determining turbidity of said liquid based upon a ratio formed by said measured amount of transmitted light and said measured second amount of light scatter; and,
    resolving ambiguity in said turbidity based upon said measured first amount of light scatter.

7. A method for determining quality of petroleum oil comprising the steps of:
    transmitting a light beam into said petroleum oil from a light source;
    measuring an amount of perpendicular scatter light of said transmitted light;
    measuring an amount of back scatter light of said transmitted light;
    determining turbidity of said petroleum oil based upon said measured amount of back scatter light; and,
    determining the presence of antifreeze in said petroleum oil based upon said measured amount perpendicular scatter light.

8. A method in accordance with claim 7, further comprising the steps of:
    measuring an amount of transmitted light at a point substantially directly across from said light source; and,
    determining turbidity of said petroleum oil based upon said measured amounts of transmitted light and back scatter light.

9. A method in accordance with claim 8, wherein said step of determining turbidity comprises the step of determining turbidity of said petroleum oil based upon a ratio of said measured amounts of transmitted light and back scatter light.

10. A method of determining the quality of a liquid comprising:
    transmitting light into the liquid;
    measuring a direct amount of the light passing directly through the liquid;
    measuring a perpendicularly scattered amount of the light scattered by the liquid at substantially a right angle to the light passing directly through the liquid;
    measuring a back scattered amount of the light scattered by the liquid at an acute angle with respect to the light passing directly through the liquid;
    forming a turbidity ratio based on the direct amount and the back scattered amount; and,
    resolving ambiguities in the turbidity ratio using the perpendicularly scattered amount.

11. The method of claim 10 wherein the resolving of the ambiguities in the turbidity ratio comprises resolving the ambiguities in the turbidity ratio without forming a ratio based on the perpendicularly scattered amount.

12. The method of claim 10 wherein the liquid is a petroleum oil.

13. The method of claim 12 wherein the ambiguities are caused by water and antifreeze in the petroleum liquid.

14. The method of claim 10 wherein the acute angle is less than or equal to about 48 degrees.

* * * * *